United States Patent [19]

Schumann

[11] Patent Number: Plant 5,941

[45] Date of Patent: Apr. 14, 1987

[54] GERANIUM PLANT NAMED SATELLITE

[75] Inventor: Ingeborg Schumann, Bad Ems, Fed. Rep. of Germany

[73] Assignee: Fischer Geraniums, Inc., Netherlands Antilles

[21] Appl. No.: 761,100

[22] Filed: Jul. 31, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Satellite having salmon flowering startel flower type with strong divided petals; novel, decorative zonal foliage; compact growth habit with good branching; early flowering response, and heavy flower yield.

2 Drawing Figures

The present invention comprises a new and distinct cultivar of geranium, botanically known as *Pelargonium zonale,* and hereinafter referred to by the cultivar name Satellite.

Satellite is a product of a planned breeding program which had the objective of creating new geranium cultivars having novel startel flower type, unique leaf shape, salmon flower color and single flower form.

Satellite was originated from a hybridization made by Ingeborg Schumann in a controlled breeding program in Hillscheid, Federal Republic of Germany in 1981. The female parent was an inbred line of Stellar Artic Star with Salmon Sprinter. The male parent of Satellite was an inbred line of Stellar Orange with Startel Salmon. Both parents are unpatented.

Satellite was discovered and selected as one flowering plant within the progeny of the stated cross by Ingeborg Schumann on Aug. 26, 1982 in a controlled environment in Hillscheid, Federal Republic of Germany.

The first act of asexual reproduction of Satellite was accomplished when vegetative cuttings were taken from the initial selection in January of 1983 in a controlled environment in Hillscheid, Federal Republic of Germany by a technician working under formulations established and supervised by Ingeborg Schumann. Horticultural examination of selected units initiated in the spring of 1983 and 1984 has demonstrated that the combination of characteristics as herein disclosed for Satellite are firmly fixed and are retained through successive generations of asexual reproduction.

Satellite has not been observed under all possible environmental conditions. The phenotype may vary significantly with variations in environment such as temperature, light intensity, and day length. The following observations, measurements and comparisons describe plants grown in Hillscheid, Federal Republic of Germany, under conditions which approximate those generally used in commercial practice.

The following traits have been repeatedly observed and are determined to be basic characteristics of Satellite, which in combination distinguish this geranium as a new and distinct cultivar.

1. Salmon flowers with startel flower type; divided petals are strong.
2. Novel leaf shape; very decorative.
3. Compact habit with good branching.
4. Very dark zonation.

5. Early flowering response, and heavy flower production in spring and summer.

The accompanying photographic drawings shows typical flower and foliage characteristics of Satellite, with colors being as true as possible with illustrations of this type.

Sheet 1 is a color photograph showing Satellite in perspective view.

Sheet 2 is a black and white print showing the novel leaf shape of Satellite, at three stages of growth.

In the following description color references are made to The Royal Horticultural Society Colour Chart. The color values were determined between 2:00 p.m. and 3:00 p.m. on May 15, 1985 under 20,000 Lux light intensity at Hillscheid, Federal Republic of Germany.

Classification:

*Botanical.*—A hybrid of the genus Pelargonium l'hert and species *Pelargonium zonale.*

*Commercial.*—Satellite.

INFLORESCENCE

A. Umbel:

*Average diameter.*—83 mm.

*Average depth.*—44 mm.

*Peduncle length.*—166 mm.

*Pedicel length.*—25 mm.

B. Corolla:

*Average diameter.*—42 mm.

*Form.*—Single flower, generally star shaped; petals have relatively sharp tips.

*Color (general tonality from a distance of three meters).*—Salmon. Upper surface: Mainly 32C, lighter near margin, approximately 29D; center of petal darker, approximately 32B.

C. Bud:

*Shape.*—Elongated, flat top.

*Color.*—Yellow-white to light salmon.

D. Reproductive organs:

*Androecium.*—7 anthers.

*Gynoecium.*—4–5 lobed stigma.

E. Spring flowering response period: In Hillscheid, Federal Republic of Germany, in 1983, 95% of plants opened with at least one flower 13 weeks after planting of unrooted cuttings.

F. Outdoor flower production: The total flower count in 1983 in Hillscheid, Federal Republic of Germany, was between 75 and 85 flowers per plant for the June through October observation period.

G. Durability: Good.

PLANT

A. Foliage:

*Form.*—Somewhat similar to oak leaf, but not as long.

*Margin.*—Deeply indented, forming leaf segments; leaf tips relatively pointed.

*Color.*—Top surface: Medium green, approximately 137B–C. Zonation: Strong brown zonation, primarily near margin of leaves.

*Tolerance of botrytis.*—Good.

B. General appearance and form:

*Internode length.*—21 mm.

*Branching pattern.*—4.4 branches within a period of 13 weeks cultivation from unrooted cuttings.

*Height.*—280 mm.

I claim:

1. A new and distinct cultivar of geranium named Satellite, as described and illustrated, and particularly characterized by its salmon flowering startel flower type, with strong divided petals; novel, decorative zonal foliage; compact growth habit with good branching; early flowering response, and its heavy flower yield.

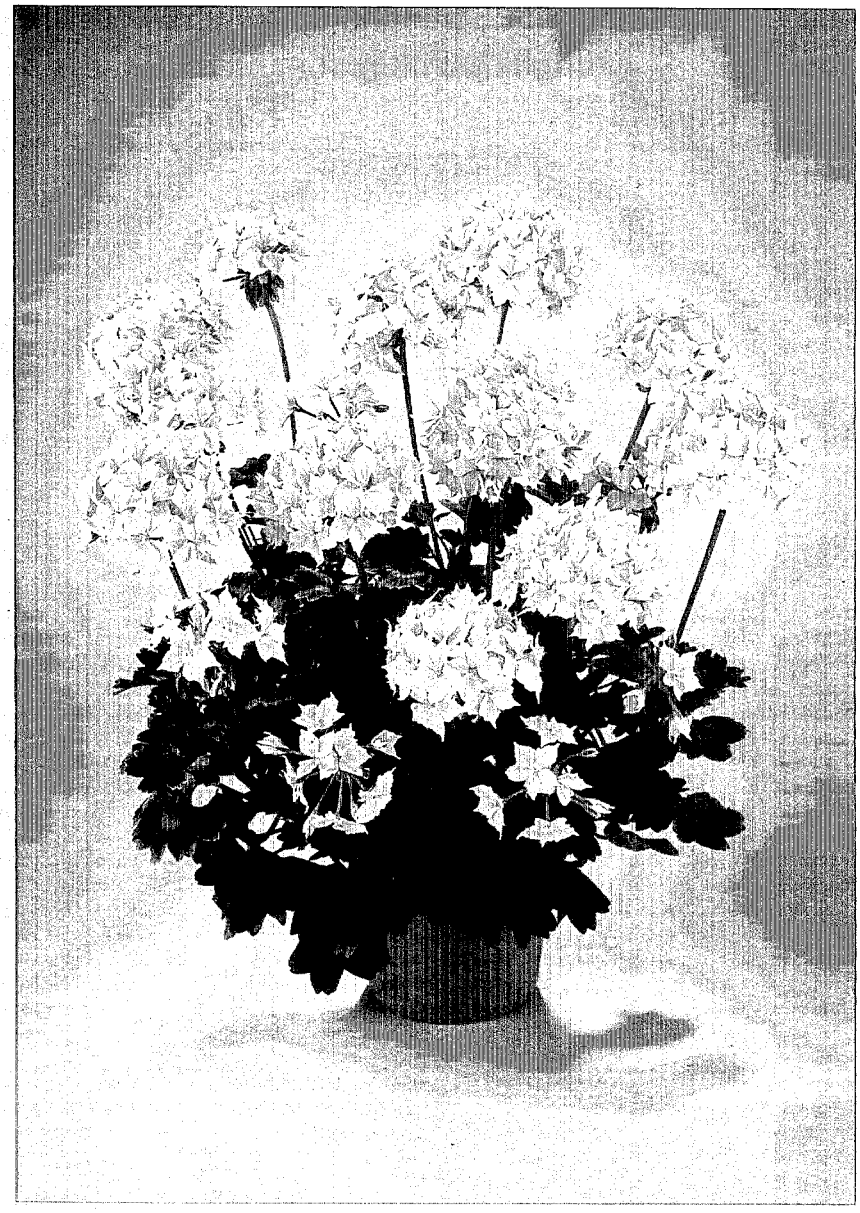

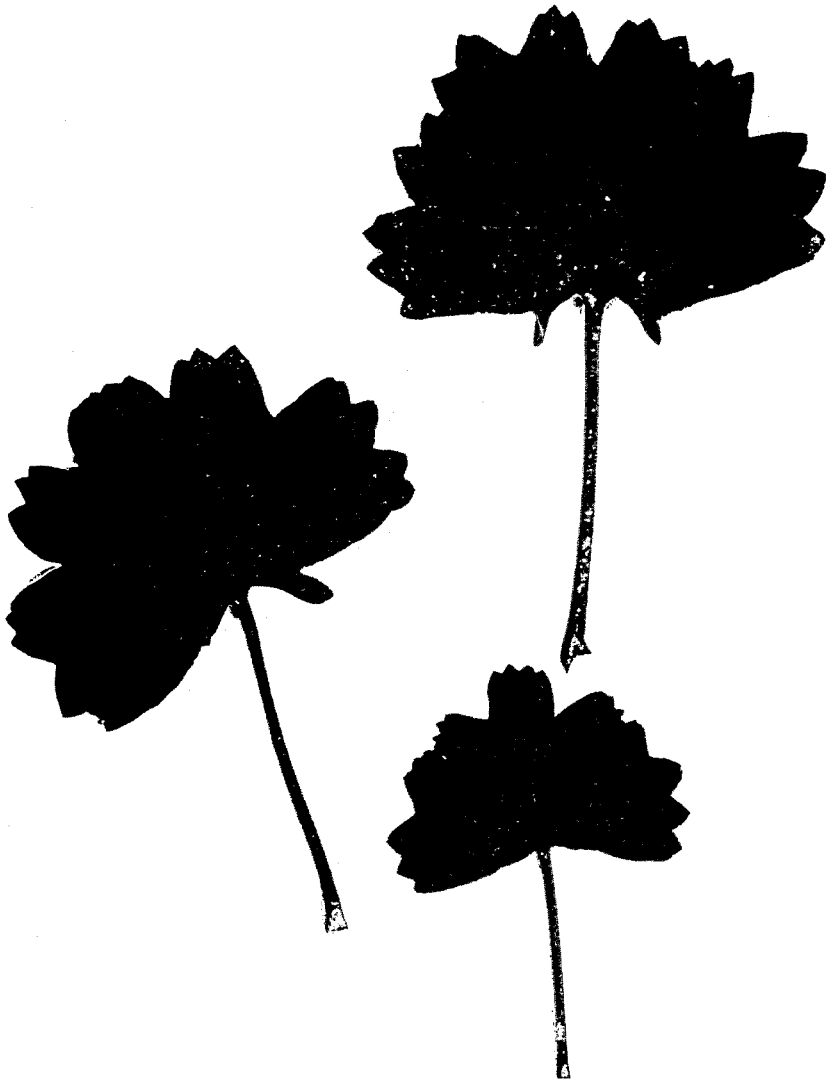

* * * * *